US008481730B2

(12) United States Patent
Rao et al.

(10) Patent No.: US 8,481,730 B2
(45) Date of Patent: Jul. 9, 2013

(54) METHOD OF SYNTHESIS OF BOSENTAN, ITS POLYMORPHIC FORMS AND ITS SALTS

(75) Inventors: Dharmaraj Ramachandra Rao, Maharashtra (IN); Rajendra Narayanrao Kankan, Maharashtra (IN); Manjinder Singh Phull, Maharashtra (IN); Ashwini Amol Sawant, Mulund (IN)

(73) Assignee: CIPLA Limited, Mumbai (IN)

( * ) Notice: Subject to any disclaimer, the term of this patent is extended or adjusted under 35 U.S.C. 154(b) by 105 days.

(21) Appl. No.: 12/811,279

(22) PCT Filed: Jan. 2, 2009

(86) PCT No.: PCT/GB2009/000009
§ 371 (c)(1),
(2), (4) Date: Oct. 4, 2010

(87) PCT Pub. No.: WO2009/083739
PCT Pub. Date: Jul. 9, 2009

(65) Prior Publication Data
US 2011/0015394 A1    Jan. 20, 2011

(30) Foreign Application Priority Data

Jan. 1, 2008 (IN) .............................. 12/MUM/2008
Apr. 9, 2008 (IN) ........................... 836/MUM/2008

(51) Int. Cl.
*C07D 403/04* (2006.01)
*C07D 239/69* (2006.01)
*A61K 31/506* (2006.01)
*A61P 9/12* (2006.01)

(52) U.S. Cl.
USPC .......................................... 544/296; 514/269

(58) Field of Classification Search
USPC .......................................... 544/296; 514/269
See application file for complete search history.

(56) References Cited

U.S. PATENT DOCUMENTS 5,292,740 A * 3/1994 Burri et al. ..................... 514/256
6,136,971 A * 10/2000 Harrington et al. ........... 544/122
8,288,401 B2 * 10/2012 Gaitonde et al. .............. 514/269

FOREIGN PATENT DOCUMENTS

| CA | 2071193 | 8/1998 |
| WO | WO 01/55120 A1 | 8/2001 |
| WO | WO 2008/135795 A2 | 11/2008 |
| WO | WO 2009/004374 A1 | 1/2009 |
| WO | 2009047637 A1 | 4/2009 |
| WO | 2009053748 A2 | 4/2009 |
| WO | 2009093127 A2 | 7/2009 |
| WO | WO 2009/083739 A1 | 7/2009 |

OTHER PUBLICATIONS

Harada et al. Bioorg. Med. Chem. 9 (2001) 2955-2968.*
Foreign communication from a related counterpart application—International Preliminary Report on Patentability, PCT/GB2009/000009, Jul. 6, 2010, 12 pages.
Foreign communication from a related counterpart application—International Search Report and Written Opinion, PCT/GB2009/000009, May 29, 2009, 20 pages.
Harada, Hironori, et al., "Ethenesulfonamide and ethanesulfonamide derivatives, a novel class of orally active endothelin-a receptor antagonists," Bioorganic & Medicinal Chemistry, May 19, 2009, vol. 9, pp. 2955-2968.
Foreign communication from a related counterpart application—European Examination Report, EP 09700123.4 dated Dec. 6, 2012, 6 pages.

* cited by examiner

*Primary Examiner* — Venkataraman Balasubramanian
(74) *Attorney, Agent, or Firm* — Conley Rose, P.C.; Rodney B. Carroll

(57) ABSTRACT

The present invention relates to alkaline earth metal salts of bosentan, anyhdrous bosentan, polymorphic forms thereof, amorphous bosentan and processes for preparing them. The present invention further relates to a process for the preparation of bosentan and its pharmaceutically acceptable salts.

35 Claims, 7 Drawing Sheets

METHOD OF SYNTHESIS OF BOSENTAN, ITS POLYMORPHIC FORMS AND ITS SALTS

CROSS-REFERENCE TO RELATED APPLICATIONS

This application is a filing under 35 U.S.C. 371 of International Application No. PCT/GB2009/000009 filed Jan. 2, 2009, entitled "Method of Synthesis of Bosentan, Its Polymorphic Forms and Its Salts," claiming priority of Indian Patent Application Nos. 12/MUM/2008 filed Jan. 1, 2008 and 836/MUM/2008 filed Apr. 9, 2008, which applications are incorporated by reference herein in their entirety.

FIELD OF INVENTION

The present invention relates to alkaline earth metal salts of bosentan, anhydrous bosentan, polymorphic forms thereof, amorphous bosentan, and processes for preparing them. The present invention further relates to a process for the preparation of bosentan and its pharmaceutically acceptable salts.

BACKGROUND OF INVENTION

Bosentan, one of the compounds disclosed in CA2071193 and its equivalent U.S. Pat. No. 5,292,740, belongs to an important class of sulfonamides having endothelin inhibiting activity useful in treatment of hypertension, ischemia, and related diseases.

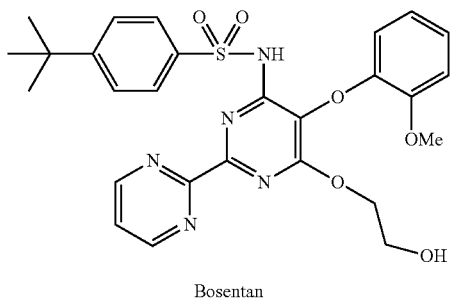 [SMILES: COc1ccccc1Oc1c(NS(=O)(=O)c2ccc(C(C)(C)C)cc2)nc(-c2ncccn2)nc1OCCO]

Bosentan

U.S. Pat. No. 5,292,740 further discloses a process for preparation of bosentan comprising diethyl bromomalonate and guaiacol as the reactants. The final step of the process is the reaction of substituted pyrimidine monohalide derivative with ethylene glycol in the presence of sodium hydroxide to give bosentan. In this step, coupling of two molecules of pyrimidine monohalide derivative with one molecule of ethylene glycol generates undesirable impurities, such as the dimeric impurities, as the by-products. Multiple crystallization and purification steps are required to lower the amounts of these impurities. Also, the process requires use of excess of ethylene glycol which makes it costly and difficult to handle on industrial scale.

U.S. Pat. No. 6,136,971 describes an alternate process for the preparation of bosentan which uses monoprotected ethylene glycol. The process comprises reacting a substituted pyrimidine monohalide derivative with ethylene glycol mono t-butyl ether in the presence of sodium hydroxide in toluene to give a t-butyl ether derivative which is deprotected with formic acid in toluene to give a 2-(formyloxy)ethoxy derivative. Finally, removal of the formyl group by treatment with aqueous sodium hydroxide yields bosentan. The process requires additional steps of protection and deprotection of ethylene glycol that makes the process laborious and expensive.

In the processes of the prior art, the reaction of a substituted pyrimidine monohalide derivative with unprotected/protected ethylene glycol either generate undesirable impurities, for example, dimer impurities up to an amount of 10%, and thus require a number of purification and isolation steps to remove impurities or they require protection and deprotection of ethylene glycol which is time consuming and not feasible industrially.

Secondly, the essential feature of the reaction of substituted pyrimidine monohalide derivative with ethylene glycol is the use of a base, specifically a strong inorganic base, i.e., sodium hydroxide. It is found that the reaction does not proceed in the presence of an organic base, such as triethylamine or N-ethyldiisopropyl amine. The prior art indicates that the reaction proceeds only in the presence of a strong inorganic base. But, the use of a strong base produces undesirable impurities which affects the yield and purity of the product.

Therefore, there remains a need in the art for an improved process which is able to overcome the shortcomings of the prior art processes. Also, there is a need for a process that is simple for industrial scale up, and which requires fewer purification and isolation steps thereby obtaining the bosentan in good yield and purity.

Bosentan is marketed under the brand name Tracleer® by Actelion Pharmaceuticals. The active ingredient in Tracleer® is bosentan monohydrate which has a water content of about 3-5%.

Generally, an ideal candidate for any type of pharmaceutical formulation is an active ingredient which is non-hygroscopic in nature. The presence of any amount of moisture can lead to the formation of agglomerates, lumps, and impurities in any formulation. Thus, it is not always suitable to have an active ingredient having a high moisture content.

OBJECT OF THE INVENTION

A primary object of the present invention is to provide a method for synthesis of bosentan and its pharmaceutically acceptable salts.

Another object of the present invention is to provide novel, stable, forms of bosentan, in particular novel salts of bosentan and novel anhydrous forms of bosentan.

SUMMARY OF THE INVENTION

According to a first aspect of the present invention, there is provided an alkaline earth metal salt of bosentan. In an embodiment, the salt is the barium salt. In another embodiment, the salt is the calcium salt.

According to another aspect of the present invention, there is provided anhydrous bosentan.

According to another aspect of the present invention, there is provided anhydrous Form B bosentan. Anhydrous bosentan Form B may be characterised by having an XRPD pattern comprising peaks at 9.6, 16.1, 17.1, 18.4 and 21.8° 2θ±0.2°2θ. Form B may also be characterised by having an XRPD pattern comprising peaks at 9.6, 12.3, 14.8, 16.1, 17.1, 17.5, 18.4, 21.1, 21.8, 22.1 and 22.8° 2θ±0.2°2θ.

Figure 1:
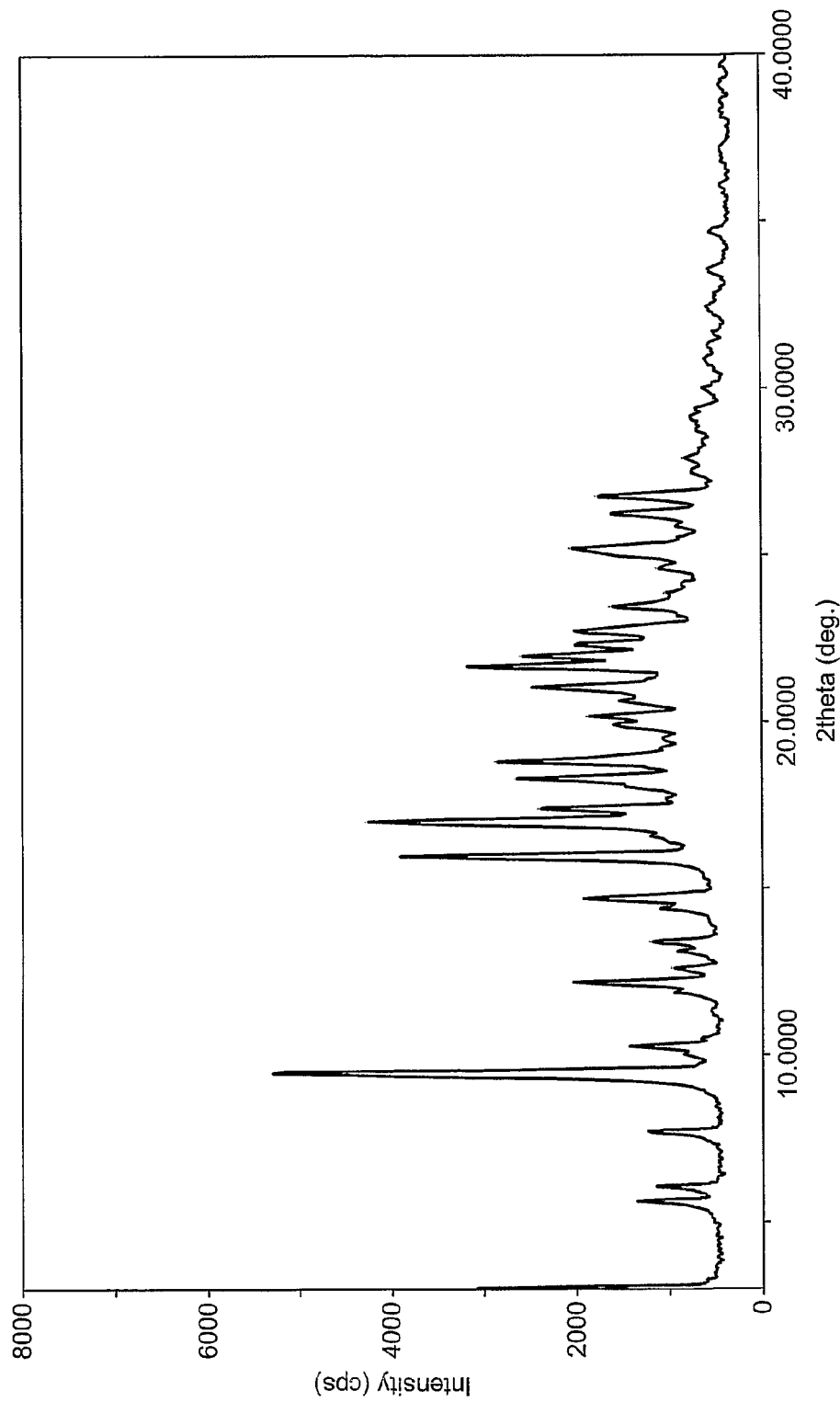
FIG. 1 depicts an X-ray diffraction spectrum of anhydrous bosentan Form B.

In an embodiment, anhydrous bosentan Form B is characterised by having the XRPD pattern as shown in FIG. 1.

Figure 2:
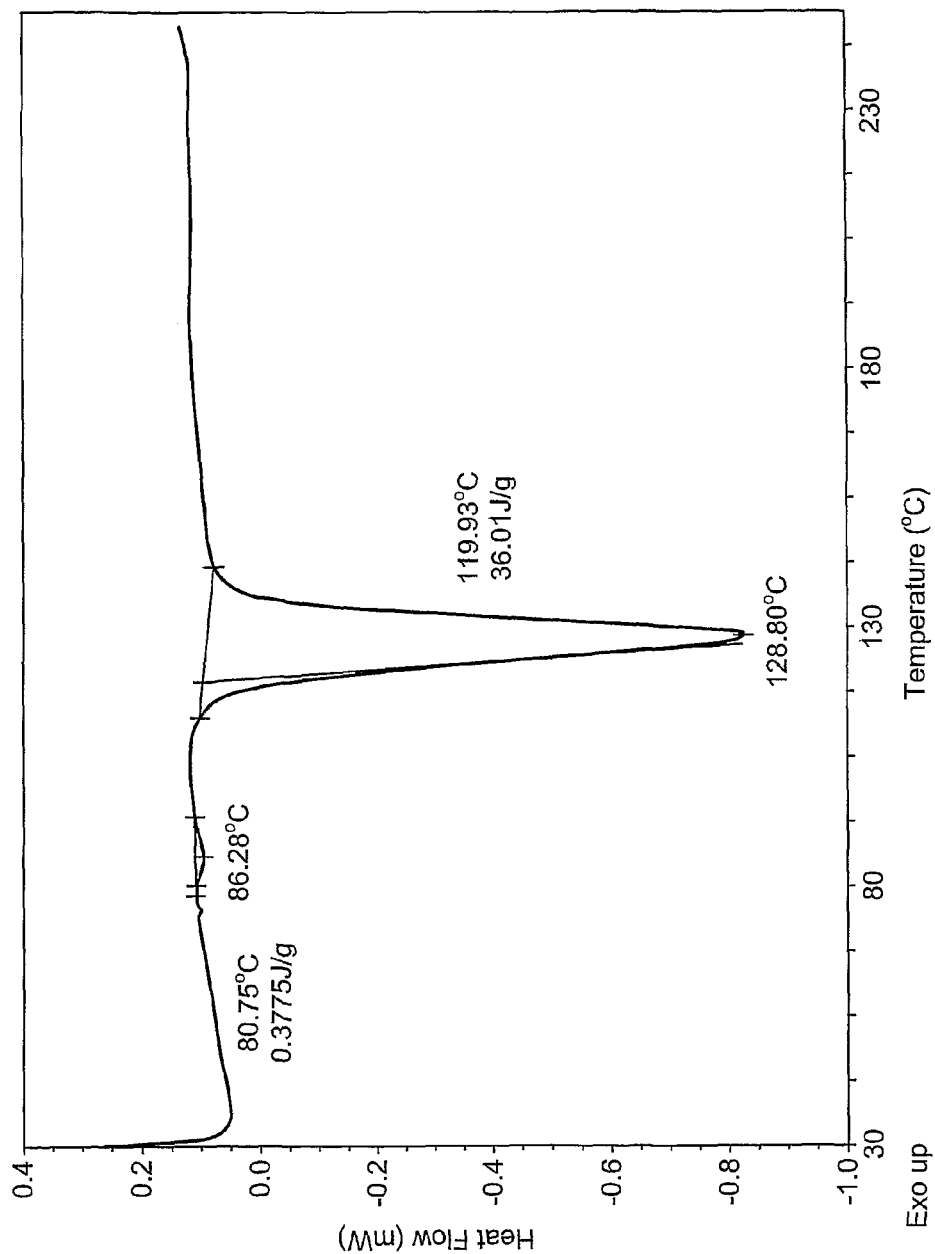
FIG. 2 depicts a differential scanning calorimetric thermogram of anhydrous bosentan Form B.

Anhydrous bosentan Form B may also be characterised by having a DSC thermogram as shown in FIG. 2.

Figure 3:
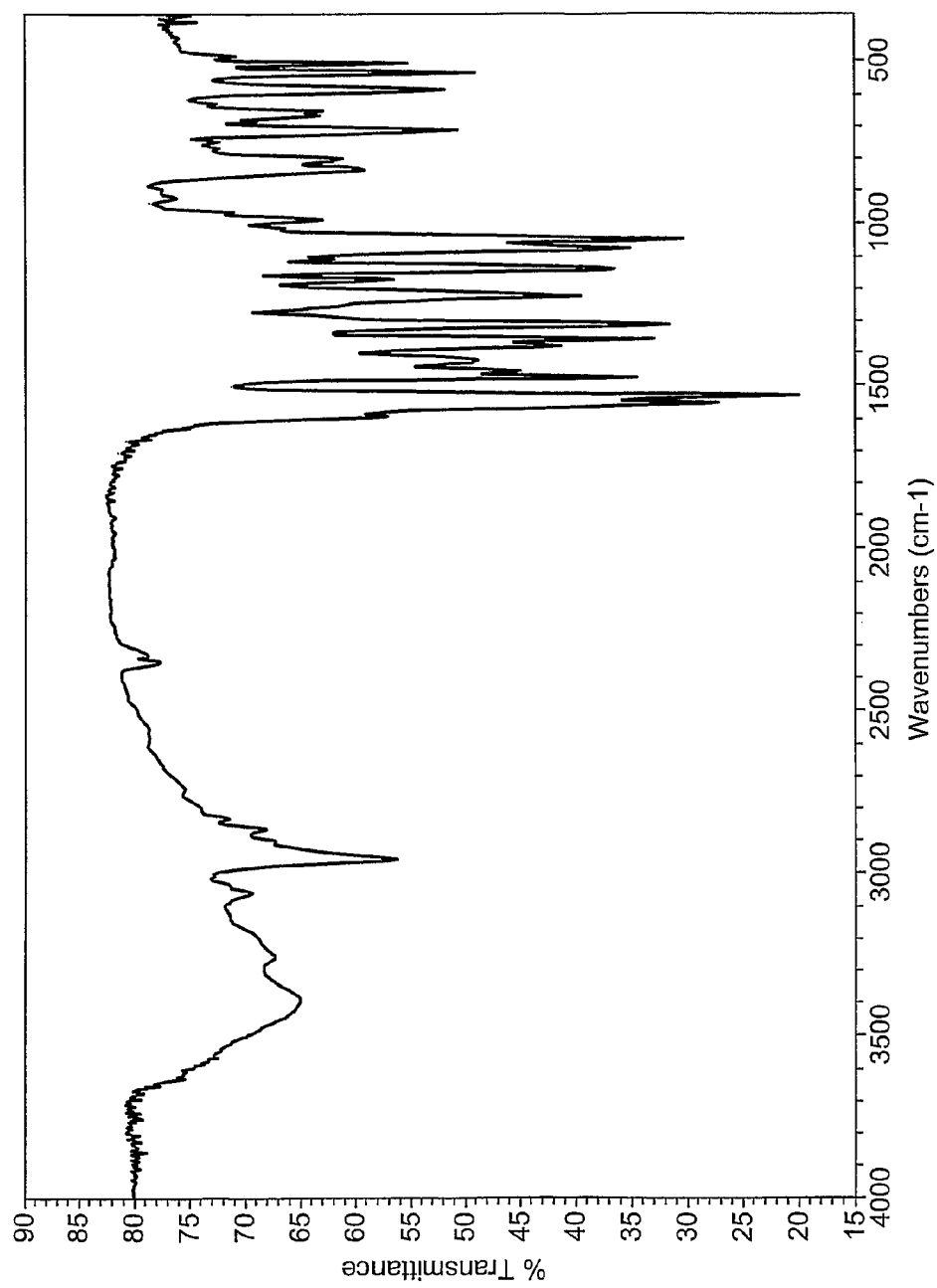
FIG. 3 depicts an Infra-red absorption spectrum of anhydrous bosentan Form B.

Anhydrous bosentan Form B may also be characterised by having an IR spectrum as shown in FIG. 3.

According to another aspect of the present invention, there is provided anhydrous Form C bosentan. Anhydrous bosentan Form C may be characterised by having an XRPD pattern with peaks at 9.3, 15.2, 15.5, 16.7, 18.6 and 22.7° 2θ±0.2° 2θ. Form C may also be characterised by having an XRPD pattern with peaks at 9.3, 15.2, 15.5, 16.7, 18.6, 20.3, 21.3 and 22.7° 2θ±0.2° 2θ.

Figure 4:
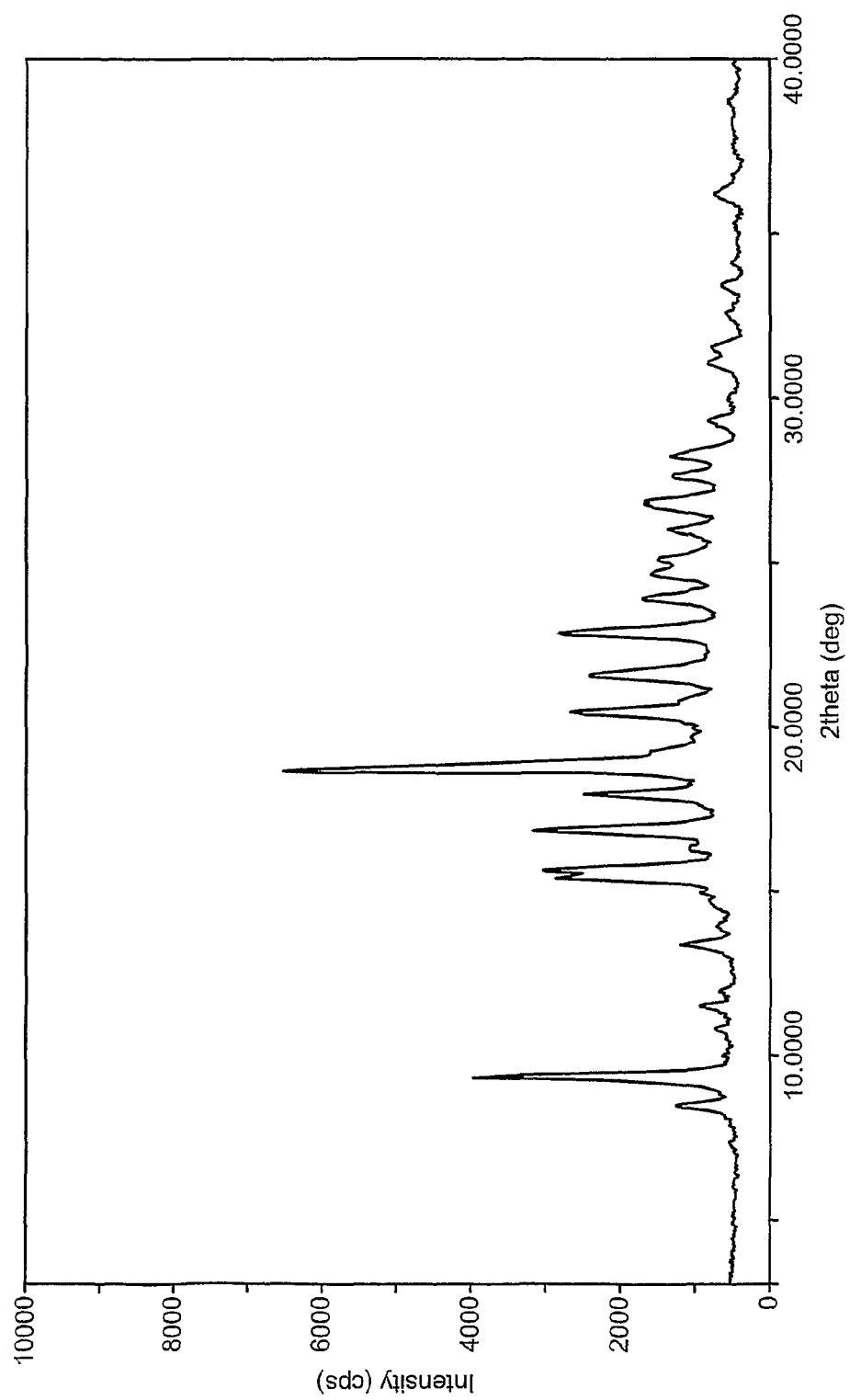
FIG. 4 depicts an X-ray diffraction spectrum of anhydrous bosentan Form C.

In an embodiment, anhydrous bosentan Form C is characterised by having the XRPD pattern as shown in FIG. 4.

Figure 5:
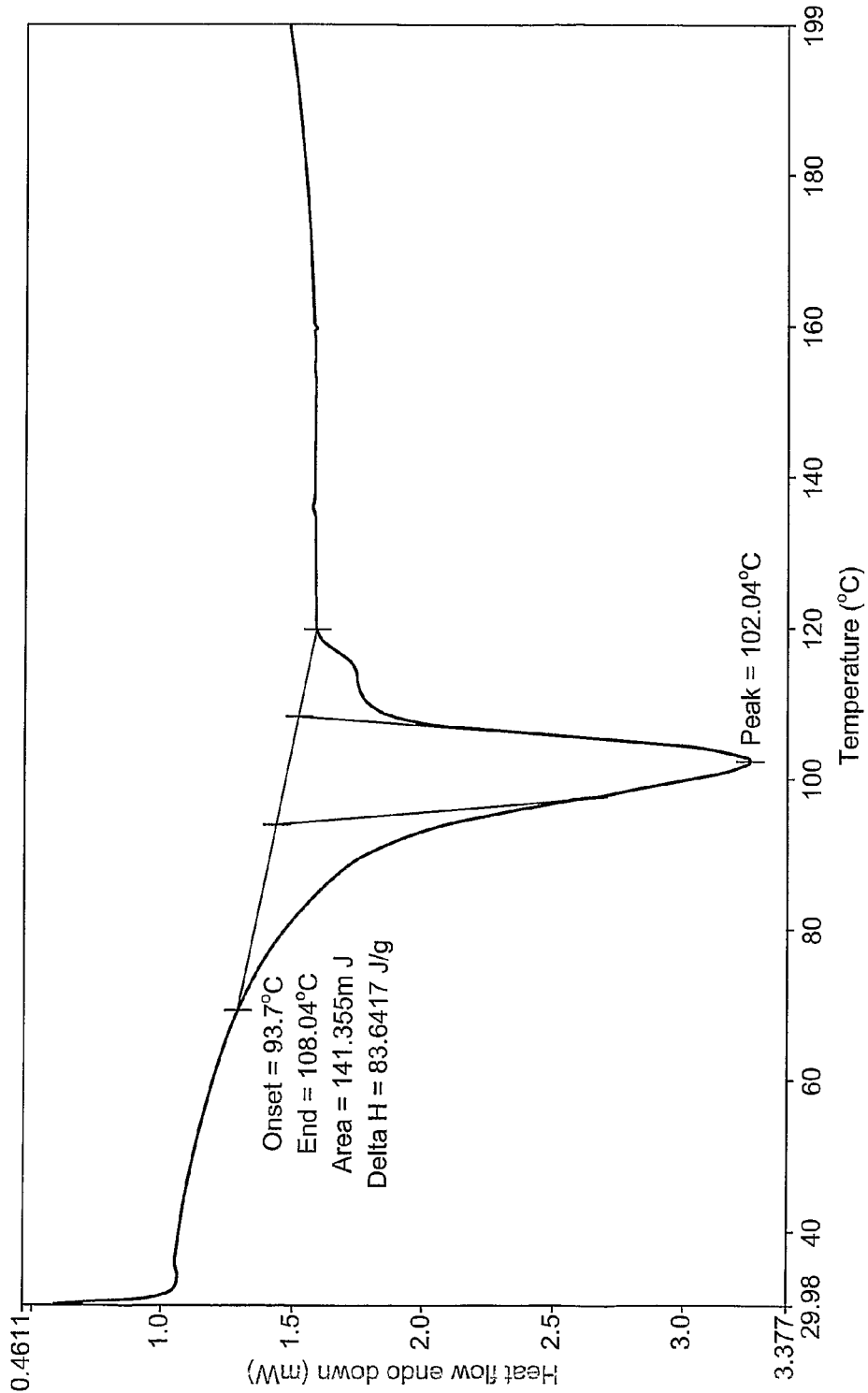
FIG. 5 depicts a differential scanning calorimetric thermogram of anhydrous bosentan Form C.

Anhydrous bosentan Form C may also be characterised by having a DSC thermogram as shown in FIG. 5.

Figure 6:
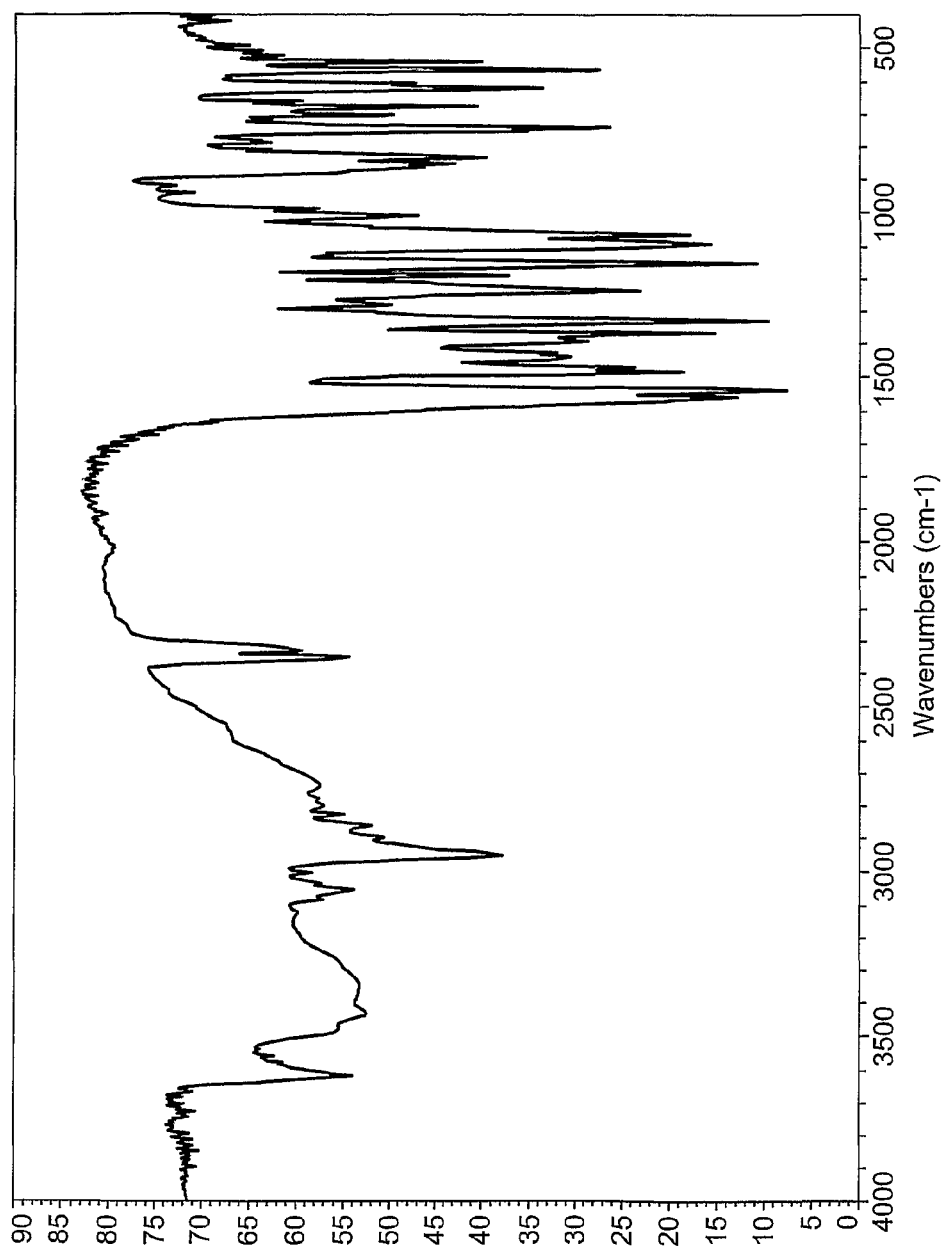
FIG. 6 depicts an Infra-red absorption spectrum of anhydrous bosentan Form C.

Anhydrous bosentan Form C may also be characterised by having an IR spectrum as shown in FIG. 6.

Figure 7:
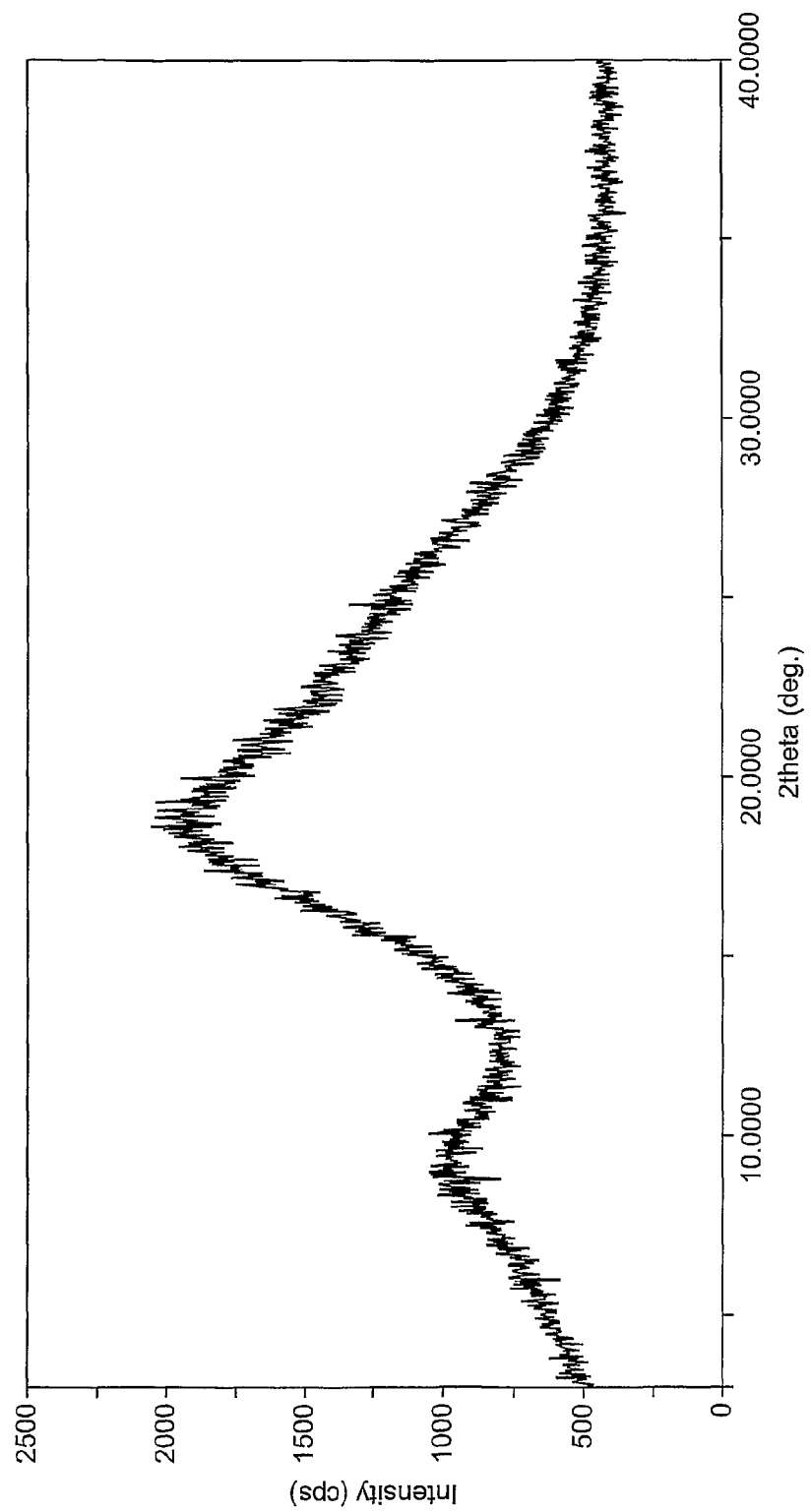
FIG. 7 depicts an X-ray diffraction spectrum of amorphous bosentan Form A.

According to another aspect of the present invention, there is provided amorphous bosentan Form A. In an embodiment, amorphous bosentan Form A is characterised by having an XRPD pattern as shown in FIG. 7.

According to another aspect of the present invention, there is provided a process for preparing bosentan or a salt thereof comprising coupling p-tert-butyl-N-[6-chloro-5-(2-methoxy-phenoxy)-[2,2'-bipyrimidin]-4-yl]benzenesulfonamide or a salt thereof with ethylene glycol in the presence of a base selected from an alkaline earth metal hydroxide.

In an embodiment, the p-tert-butyl-N-[6-chloro-5-(2-methoxy-phenoxy)-[2,2'-bipyrimidin]-4-yl]benzenesulfonamide is in the form of the potassium salt.

Suitably, the base is magnesium hydroxide, calcium hydroxide, strontium hydroxide or barium hydroxide. Preferably, the base is barium hydroxide or calcium hydroxide. More preferably, the base is barium hydroxide.

In an embodiment, the base is present in a sub-molar quantity. Suitably, the base is present in an amount ranging from about 0.1 mol % to an amount up to, but not including, 1 mol %, for example, up to, but not including, 0.9 mol %.

The coupling may be carried out in the presence of a non-polar solvent. The solvent may be selected from diglyme, tetrahydrofuran, 2-methyltetrahydrofuran, toluene or xylene. Preferably, the solvent is toluene.

In an embodiment, the product of the coupling step is isolated to form an alkaline earth metal salt of bosentan. The salt may be the magnesium, calcium, strontium or barium salt. Preferably, the salt is the barium salt or the calcium salt. More preferably, the salt is the barium salt.

In an embodiment, the product of the coupling step is converted to bosentan. The conversion may comprise adding water to the reaction mass of the coupling step and adjusting the pH of the solution to a value ranging from 1 to 2 typically using an aqueous solution of HCl. The bosentan may be isolated by extracting the crude bosentan using an extraction solvent selected from dichloromethane, ethyl acetate and toluene. The solvent may be distilled to obtain a residue. To this residue, an antisolvent selected from: methanol; ethanol; isopropanol; butanol; mixtures thereof with water (i.e., methanol-water, or ethanol-water, isopropanol-water or butanol-water) or an N,N-dimethylformamide-water mixture is added whereby bosentan precipitates. The precipitated bosentan may be isolated and dried. In this embodiment, the product is bosentan monohydrate, as known from the prior art. Preferably, the extraction solvent is dichloromethane. Preferably, the antisolvent is a 1:1 mixture of ethanol and water.

In another embodiment, the antisolvent is selected from: tetrahydrofuran; heptane; n-hexane; and methanol, the mixture of the bosentan and antisolvent is heated to the reflux temperature of the solvent mixture, the mixture is cooled to 25° C. whereby product precipitates. In an embodiment, the precipitated product is isolated. In this embodiment, the product is anhydrous bosentan Form B. Preferably, the antisolvent is heptane.

In another embodiment, the mixture of the bosentan and antisolvent is heated to the reflux temperature of the solvent mixture, then cooled to a temperature ranging from 20° C. to 30° C. whereby the anhydrous bosentan Form B precipitates. Suitably, the precipitated product is isolated and dried at a temperature above 60° C., preferably above 65° C.

The solvent may be an organic solvent, suitably selected from dichloromethane, ethyl acetate or toluene. Preferably, the solvent is ethyl acetate. The antisolvent may be selected from tetrahydrofuran, heptane, n-hexane, and methanol, more preferably heptane.

According to another aspect of the present invention, there is provided a process for preparing anhydrous bosentan Form B, the process comprising adding bosentan to a mixture of a solvent and an antisolvent, heating the mixture to the reflux temperature of the solvent mixture and cooling the mixture to a temperature ranging from around 20° C. to around 30° C. whereby the anhydrous bosentan Form B precipitates. Suitably, the mixture is cooled to a temperature of around 25° C. Typically, the precipitated product is isolated and dried at a temperature above 60° C.

The solvent may be an organic solvent, suitably selected dichloromethane, ethyl acetate or toluene. Preferably, the solvent is ethyl acetate. The antisolvent may be selected from tetrahydrofuran, heptane, n-hexane, and methanol, more preferably heptane.

The bosentan starting material may be prepared according to any one of the processes described above. The bosentan may also have been prepared according to a prior art process.

According to another aspect of the present invention, there is provided a process for preparing anhydrous bosentan Form C, the process comprising refluxing bosentan in methanol, cooling the solution to a temperature below 50° C. whereby the anhydrous bosentan Form C precipitates. Suitably, the solution is cooled to a temperature ranging from about 20° C. to about 30° C., preferably to around 25° C.

In an embodiment, the precipitated bosentan Form C is isolated and dried at a temperature above 60° C., preferably above 65° C.

The bosentan starting material may be prepared according to any one of the processes described above. The bosentan may also have been prepared according to a prior art process.

According to another aspect of the present invention, there is provided a process for preparing amorphous bosentan Form A, the process comprising concentrating a solution of crude bosentan in a solvent selected from dichloromethane, ethyl acetate and toluene to obtain a residue and adding an antisolvent to the residue whereby the amorphous bosentan Form A precipitates. Suitably, the solution is stirred after addition of the antisolvent. Preferably, the solvent is toluene.

In an embodiment, the antisolvent is selected from a hydrocarbon and an ether. Suitably, the antisolvent is hexane, heptane, diethyl ether, tetrahydrofuran or methyl tert-butyl ether. Preferably, the antisolvent is diethyl ether.

In an embodiment, the precipitated amorphous bosentan Form A is isolated and dried at a temperature above 60° C., preferably above 65° C.

The bosentan starting material may be prepared according to any one of the processes described above. The bosentan may also have been prepared according to a prior art process.

It can be seen that an alkaline earth metal hydroxide base is useful in preparing bosentan in various forms, for example, bosentan monohydrate as known from the prior art, the novel forms of bosentan described above, as well as the alkaline earth metal salts of bosentan. Thus, the present invention also provides the use of an alkaline earth metal salt in the preparation of bosentan. The various preparations are as described above.

According to another aspect of the present invention, there is provided a pharmaceutical composition comprising bosentan as described above together with one or more pharmaceutically acceptable excipients. The bosentan may be in the form of amorphous Form A bosentan, anhydrous Form B bosentan or anhydrous Form C bosentan. Such pharmaceutical excipients and compositions are well known to those skilled in the art.

According to another aspect of the present invention, there is provided the use of bosentan as described above in medicine.

According to another aspect of the present invention, there is provided the use of bosentan as described above in treating hypertension or ischemia.

According to another aspect of the present invention, there is provided a method of treating hypertension or ischemia, the method comprising administering to a patient in need thereof a therapeutically effective amount of bosentan as described above.

DETAILED DESCRIPTION OF THE INVENTION

The present invention describes a simple, economical and easy scale-up process for the synthesis of bosentan and its pharmaceutically acceptable salts which results in good yield and a high purity product.

The process for the preparation of bosentan according to the present invention comprises: coupling of p-tert-butyl-N-[6-chloro-5-(2-methoxy-phenoxy)-[2,2'-bipyrimidin]-4-yl]benzenesulfonamide (I) or a salt thereof with ethylene glycol in the presence of a weak base.

The salt of p-tert-butyl-N-[6-chloro-5-(2-methoxy-phenoxy)-[2,2'-bipyrimidin]-4-yl]benzenesulfonamide may be an alkali metal salt, for example, the sodium salt. Alternatively, the salt may be the potassium salt.

The weak base used in the above process is an alkali earth metal hydroxide. The alkali earth metal hydroxide may be barium hydroxide, calcium hydroxide, strontium hydroxide, and magnesium hydroxide, more preferably barium hydroxide. The quantity of alkali earth metal hydroxide required for the process ranges from a catalytic amount to an amount that is the molar equivalent. Most preferably, the alkali earth metal hydroxide is used in sub-molar quantities. For example, the alkali earth metal hydroxide may be used in an amount from about 0.1 mol % to an amount up to, but not including, 1 mol %, suitably 0.1 mol % to 0.9 mol %.

The coupling reaction takes place in the presence of a suitable organic solvent. The suitable organic solvent may be a non-polar solvent selected from: an ether such as diglyme or tetrahydrofuran or 2-methyltetrahydrofuran; or a hydrocarbon solvent such as toluene or xylene. Most preferably, the organic solvent used in the process of present invention is toluene. The reaction mass is heated at a temperature ranging from about 100° C. to about 120° C., preferably at a temperature of around 110° C.

In an embodiment, all the base to be used in the reaction is added in one go. Alternatively, the base is added to the reaction mass in lots. In other words, one amount of base is added to the reaction mass, the reaction allowed to progress then another amount of base is added to the reaction mass, with each amount of base representing a "lot." The base may be added in two, three or four lots, preferably two lots. The amounts of the base in each lot may be in any proportion, preferably equal proportions, i.e., the same amount of base is added in each lot. Preferably, two lots of equal amounts are added. It has surprisingly been found that the formation of undesirable impurities may be controlled by addition of the base in lots.

After completion of the reaction, the solvent may be removed completely by distillation and water added. The pH of the resulting suspension may be adjusted in the range of 1-2 using, for example, an aqueous acid solution. Preferably, the aqueous acid solution is a mixture of hydrochloric acid and water. The resulting solid may be extracted using a suitable solvent such as dichloromethane, ethyl acetate, toluene, most preferably dichloromethane. The organic layer may be collected, washed with water and distilled off to obtain a residue. To this residue a mixture of an organic solvent and water may be added. The organic solvent may be an alcoholic solvent such as methanol, ethanol, isopropanol, butanol, more preferably ethanol or mixtures of solvents such as ethanol-water or N,N-dimethylformamide-water. The resulting suspension may be heated at the reflux temperature to obtain a clear solution which may be further cooled to a temperature of about 25° C. to provide bosentan.

The reaction scheme is represented as follows:

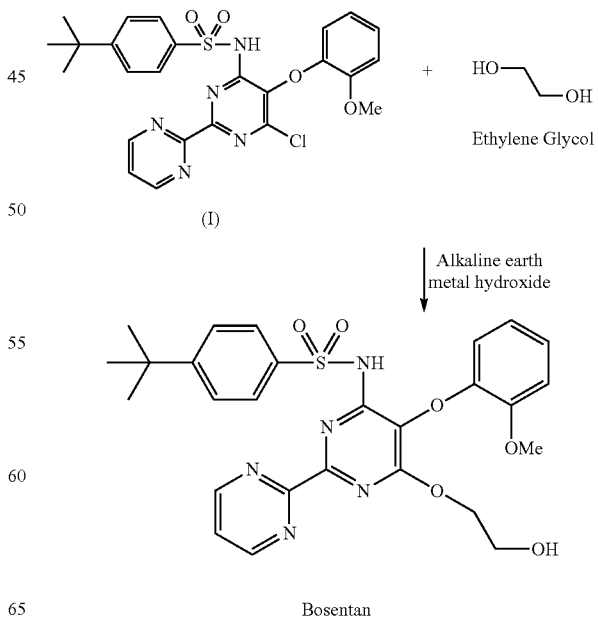

The compound of formula (I) viz. p-tert-butyl-N-[6-chloro-5-(2-methoxy-phenoxy)-[2,2'-bipyrimidin]-4-yl]benzenesulfonamide or its salt, used in the above scheme, may be prepared by any one of the processes known in the art.

Bosentan may also be isolated in the form of its alkali earth metal salt. This forms another aspect of the present invention. The preferable salts of the present invention are barium and calcium salts of bosentan.

The process for the preparation of an alkali earth metal salt comprises reaction of p-tert-butyl-N-[6-chloro-5-(2-methoxy-phenoxy)-[2,2'-bipyrimidin]-4-yl]benzenesulfonamide (I) or a salt thereof with ethylene glycol in the presence of a base. The base is a weak base and may be selected from the groups mentioned above.

The solvent used in the process may be selected from: an ether such as diglyme or tetrahydrofuran or 2-methyltetrahydrofuran; or a hydrocarbon solvent such as toluene or xylene, most preferably, toluene.

The reaction mass may be heated to a temperature ranging from about 100° C. to about 110° C. until the reaction is complete. The resulting suspension is isolated, for example, by filtration and the solid is dried to obtain the corresponding alkali earth metal salt of bosentan.

The salt of bosentan may be further purified by recrystallization with a suitable solvent or mixture of solvents. The suitable mixture of solvents is preferably methanol-isopropyl acetate.

An alkali earth metal salt prepared by the above process may be further converted to the other salts of alkaline earth metal group such as the calcium salt or alkali metal salts such as the sodium salt via formation of bosentan free base as described hereinbefore.

There are a number of advantages to the process of the present invention.

1) One of the important advantages of the process of the present invention is that it avoids the use of a strong base such as sodium hydroxide which leads to the formation of undesirable impurities. In the process of the present invention, these impurities are avoided by the use of a weak base.

2) The use of an alkali earth metal hydroxide avoids the formation of dimeric impurities thereby increasing the yields of bosentan. The other undesirable impurities can be controlled by addition of alkali earth metal hydroxide in lots.

3) The amount of alkaline earth metal hydroxide required in the process of the present invention is in sub-molar to molar quantities, preferably in sub-molar quantities.

4) The alkali earth metal salt of bosentan can be obtained without isolation of bosentan base.

5) The alkali earth metal salt of bosentan has a low solubility and hence can be easily precipitated.

6) Purification and isolation of bosentan or its alkali earth metal salt is easy and involves a small number of crystallization steps.

All these merits make the process of the present invention simple, cost effective, and industrially feasible.

According to another aspect of the present invention, there is provided anhydrous bosentan. The anhydrous bosentan is stable. The term "stable" with respect to this application refers to a compound which is non-hygroscopic and does not pick-up moisture even in a highly humid atmosphere.

Anhydrous bosentan is provided in polymorphic forms A, B and C.

Form B of bosentan may be characterized by means of its X-ray powder diffraction (XRPD) pattern and/or thermogravimetric analysis. The XRPD of anhydrous bosentan Form B has been measured on a Rigaku miniflex advance powder X-ray diffractometer using a Cu—$K_{\alpha-1}$ radiation source. The XRPD spectrum is shown in FIG. 1.

Anhydrous bosentan Form B in accordance with the present invention may be characterized by having an XRPD pattern comprising peaks at 2θ values (±0.2) of 9.6, 16.1, 17.1, 18.4 and 21.8 degrees.

In an embodiment, anhydrous bosentan Form B is further characterized by having an XRPD pattern comprising peaks at 2θ (±0.2) values of 9.6, 12.3, 14.8, 16.1, 17.1, 17.5, 18.4, 21.1, 21.8, 22.1 and 22.8 degrees.

In another embodiment, anhydrous bosentan Form B is characterized by having an XRPD pattern comprising peaks at 2θ (±0.2) values as given in Table 1 below.

TABLE 1

Anhydrous bosentan Form B

| Diffraction angles (2θ°) | Relative intensity (% I/Io) |
| --- | --- |
| 5.7 | 25 |
| 6.1 | 22 |
| 7.8 | 24 |
| 9.6 | 100 |
| 10.4 | 27 |
| 12.0 | 18 |
| 12.3 | 39 |
| 13.5 | 23 |
| 14.5 | 21 |
| 14.8 | 37 |
| 16.1 | 75 |
| 16.5 | 19 |
| 16.7 | 23 |
| 17.1 | 81 |
| 17.5 | 45 |
| 18.2 | 28 |
| 18.4 | 50 |
| 18.7 | 24 |
| 18.9 | 54 |
| 19.3 | 21 |
| 19.6 | 21 |
| 20.0 | 30 |
| 20.3 | 35 |
| 20.6 | 25 |
| 20.7 | 29 |
| 21.1 | 47 |
| 21.3 | 24 |
| 21.8 | 60 |
| 22.1 | 49 |
| 22.4 | 38 |
| 22.8 | 39 |
| 22.9 | 31 |
| 23.5 | 30 |
| 24.7 | 21 |
| 25.0 | 31 |
| 25.3 | 38 |
| 26.3 | 31 |
| 26.8 | 34 |

In another embodiment, anhydrous bosentan Form B is characterized by having an Infra-red (IR) absorption spectrum comprising characteristic peaks at 3396, 3065, 2962, 2361, 1579, 1557, 1500, 1481, 1448, 1405, 1384, 1342, 1254, 1202, 1171, 1139, 1111, 1081, 1021, 871, 835, 751, 690, 628, 576, 546, 418 cm$^{-1}$.

Anhydrous bosentan Form B of the present invention may be further characterized by having a melting point onset as determined by DSC ranging from 119° C. to 129° C.

The present invention further provides a process for the preparation of anhydrous bosentan Form B which comprises coupling p-tert-butyl-N-[6-chloro-5-(2-methoxy-phenoxy)-[2, 2'-bipyrimidin]-4-yl]benzenesulfonamide or a salt thereof with ethylene glycol in the presence of a base and a suitable organic solvent. The base used in the process may be selected from sodium hydroxide, barium hydroxide, calcium hydroxide, strontium hydroxide or magnesium hydroxide. The suitable organic solvent may be a non-polar solvent selected from an ether (such as diglyme or tetrahydrofuran or 2-methyltetrahydrofuran) or a hydrocarbon solvent (such as toluene or xylene). Preferably, the solvent is toluene. The reaction mass may be heated to a temperature ranging from 100° C. to 120° C., preferably to 110° C. The base may be added in lots, in the same manner as described above.

After completion of the reaction, the solvent may be removed completely, for example, by distillation and water may be added. The pH of the reaction mass may be adjusted to a pH value ranging from 1 to 2 using for example aqueous hydrochloric acid. The reaction mass may be extracted using a suitable solvent such as dichloromethane, ethyl acetate or toluene, most preferably dichloromethane. Further, an anti-solvent selected from tetrahydrofuran, heptane, n-hexane, and methanol, more preferably heptane may be added, the resulting solid may be filtered and dried under vacuum at a temperature above 60° C. to obtain anhydrous bosentan Form B.

Alternatively, anhydrous bosentan Form B of the present invention may be prepared by heating crude bosentan with a mixture of a suitable solvent and an antisolvent as defined above at a temperature ranging from 50° C. to 80° C. to obtain a clear solution. The solution is further cooled to a temperature ranging from 25° C. to 30° C. to obtain a solid which is dried at a temperature ranging from 60° C. to 100° C. to obtain anhydrous bosentan Form B.

The present invention further provides another anhydrous form of bosentan designated as Form C. Anhydrous bosentan Form C of the present invention may be prepared by refluxing bosentan in methanol. The reaction mass is heated to the reflux temperature of methanol, for example to about 60° C. to 65° C., to obtain a clear solution. The solution is cooled whereby a solid is obtained. This solid is then filtered, washed with methanol, and dried at a temperature ranging from 60° C. to 65° C. to obtain anhydrous bosentan Form C.

Anhydrous bosentan Form C is characterized by means of its characteristic X-ray diffraction powder (XRPD) pattern and/or thermogravimetric analysis. The XRPD of anhydrous bosentan Form C has been measured on a Rigaku miniflex advance powder X-ray diffractometer using a Cu—K$_{\alpha-1}$ radiation source. The XRPD is shown in FIG. 4.

Anhydrous bosentan Form C may be characterized by having an XRPD pattern comprising peaks with 2theta values (±0.2) of 9.3, 15.2, 15.5, 16.7, 18.6 and 22.7 degrees.

Anhydrous bosentan Form C may be further characterized by having an XRPD pattern comprising peaks with 2theta (±0.2) values of 9.3, 15.2, 15.5, 16.7, 18.6, 20.3, 21.3 and 22.7 degrees.

The anhydrous bosentan Form C may be yet further characterized by having an XRPD pattern comprising peaks with 2theta (±0.2) values as given in Table 2 below.

TABLE 2

| Anhydrous bosentan Form C | |
|---|---|
| Diffraction angles (2θ°) | Relative intensity (% I/Io) |
| 8.3 | 14 |
| 9.3 | 62 |
| 13.2 | 13 |
| 15.2 | 38 |
| 15.5 | 41 |
| 16.7 | 43 |
| 17.8 | 29 |
| 18.6 | 100 |
| 19.1 | 11 |
| 20.2 | 26 |
| 20.3 | 32 |
| 21.3 | 22 |
| 21.4 | 29 |
| 21.5 | 22 |
| 21.6 | 15 |
| 22.7 | 37 |
| 23.6 | 12 |
| 23.7 | 18 |
| 24.3 | 12 |
| 24.4 | 14 |
| 24.5 | 13 |
| 24.9 | 12 |
| 25.8 | 11 |
| 26.4 | 16 |
| 26.5 | 18 |
| 26.7 | 18 |
| 27.4 | 12 |
| 28.0 | 14 |
| 28.1 | 11 |

Anhydrous bosentan Form C of the present invention may also be characterized by having an Infra-Red (IR) absorption spectrum comprising characteristic peaks at 3628, 3440, 3064, 2961, 2836, 2360, 2340, 1579, 1558, 1503, 1488, 1453, 1405, 1383, 1342, 1291, 1253, 1203, 1171, 1111, 1083, 1021, 997, 948, 862, 843, 794, 752, 711, 686, 668, 628, 615, 574, 547, 525, 493, 418 cm$^{-1}$.

Anhydrous bosentan Form C of the present invention may be further characterized by having a melting point of 102° C. as determined by DSC.

The anhydrous forms B and C of the present invention are stable and non-hygroscopic as they do not pick-up moisture even on exposure to air.

Bosentan may be isolated by extracting the crude bosentan from the reaction mass using a suitable solvent such as ethyl acetate, dichloromethane or toluene, preferably dichloromethane. The separated organic layer may be concentrated by heating the clear solution to a temperature ranging from about 45° C. to about 50° C. to obtain a residue. This residue may be further stirred with an antisolvent selected from a suitable etheric solvent such as diethyl ether, tetrahydrofuran or methyl tert-butyl ether or a hydrocarbon solvent such as hexane or heptane and dried at a temperature above 60° C. Alternatively, a solution of bosentan monohydrate or any crystalline bosentan in a suitable solvent as described above may be concentrated to obtain a residue. The residue may be treated with an antisolvent as described above under stirring and bosentan isolated as a precipitate which is dried at a temperature above 60° C. This results in amorphous bosentan Form A. Thus, amorphous bosentan Form A forms another aspect of the present invention. Amorphous bosentan Form A may be characterized by having an XRPD pattern as shown in FIG. 7.

In yet another aspect of the present invention, bosentan may also be isolated from the reaction mass as an alkali salt such as sodium, barium or calcium salt and optionally converted into anhydrous bosentan using one of the processes of the present invention described above.

Further, bosentan monohydrate synthesized by any known processes may be converted to anhydrous or amorphous bosentan using one of the processes of the present invention described above.

The anhydrous bosentan and amorphous bosentan according to the present invention are preferably employed in a pharmaceutical composition as an active drug substance in substantially pure form. "Substantially pure" means essentially free of other forms of bosentan. The anhydrous bosentan and amorphous bosentan of the present invention can be also admixed with one or more pharmaceutical carriers. The pharmaceutical composition may be an oral dosage form such as a liquid, a suspension or an emulsion or in a solid dosage form such as a tablet, capsule, powder or granule, or in an inhalation formulation such as an aerosol or injectable, or in a parenteral dosage form, such as those suitable for transdermal administration.

EXAMPLES

The following examples, which include preferred embodiments, will serve to illustrate the practice of this invention, it being understood that the particulars shown are by way of example and for purpose of illustrative discussion of preferred embodiments of the invention.

Example 1

Bosentan 10 gms of p-tert-butyl-N-[6-chloro-5-(2-methoxy-phenoxy)-[2,2'-bipyrimidin]-4-yl]benzenesulfonamide potassium salt and barium hydroxide (1.5 gms) were charged to a reaction vessel. Ethylene glycol (30 ml) and toluene (150 ml) were added thereto. The reaction mass was heated at a temperature of 110° C. for 2 hours. Further 1.5 gms of barium hydroxide was added and heating was continued for another 4 hours. After completion of the reaction, toluene was removed by distillation and water (150 ml) was added. The pH of the reaction mass was adjusted to a value ranging from 1 to 2 with a mixture of 1:1 HCl:water and extracted in dichloromethane. The organic layer was collected and washed with water (150 ml) and the solvent was distilled off to obtain a residue. To the residue a mixture of ethanol and water (1:1) was added and stirred. The resulting suspension was heated to reflux to obtain a clear solution. The clear solution was further cooled to 25° C. to isolate bosentan. (Water content=3 to 3.5% w/w) (Yield: 6 gms)

Example 2

Bosentan Barium 5 gms of p-tert-butyl-N-[6-chloro-5-(2-methoxy-phenoxy)-[2,2'-bipyrimidin]-4-yl]benzenesulfonamide potassium salt and barium hydroxide (0.75 gms) were charged to a reaction vessel. Ethylene glycol (15 ml) and toluene (75 ml) were added thereto. The reaction mass was heated at a temperature of 110° C. for 2 hours. Further, 0.75 gms of barium hydroxide was added and heating was continued for another 4 hours. After completion of the reaction, the solid was filtered and isolated as barium salt of bosentan. It was further purified by crystallizing with a mixture of methanol and isopropyl acetate.
(Yield: 3 Gms)

Example 3

Bosentan Calcium 10 gms of p-tert-butyl-N-[6-chloro-5-(2-methoxy-phenoxy)-[2,2'-bipyrimidin]-4-yl]benzenesulfonamide potassium salt and calcium hydroxide (14.5 gms) were charged to a reaction vessel. Ethylene glycol (30 ml) and toluene (100 ml) were added to the vessel. The reaction mass was heated at a temperature of 100° C. for 5 hours or until the reaction was complete. The resulting suspension was cooled to 25° C., filtered and isolated as the calcium salt of bosentan.

Example 4

Bosentan 100 gms of p-tert-butyl-N-[6-chloro-5-(O-methoxy-phenoxy)[2,2'-bipyrimidin]-4-yl]benzenesulfonamide potassium salt and barium hydroxide (40 gms) were charged to a reaction vessel. Ethylene glycol (300 ml) and toluene (750 ml) were added thereto. The reaction mass was heated at a temperature of 110° C. for 4 hours. After completion of the reaction, toluene was removed by distillation and water (300 ml) was added. The pH of the reaction mass was adjusted to 1-2 using 1:1 HCl and extracted in dichloromethane. The organic layer was collected and washed with water (300 ml) and the solvent was distilled off to obtain bosentan as a solid.

Example 5

Bosentan Form B

Bosentan (100 gms) obtained from example 4 was treated with a mixture of ethyl acetate:heptane (1:1). The reaction mass was stirred at 80° C. to obtain a clear solution. The solution was cooled to 25° C. The resulting solid was stirred, filtered and washed with heptane (200 ml). The solid was dried at 65° C. to obtain anhydrous bosentan Form B (60 gms).

Example 6

Bosentan Form C

Bosentan (100 gms) obtained from example 4 was treated with methanol (1000 ml). The reaction mass was stirred at 60-65° C. to obtain a clear solution. The solution was cooled to 25° C. The resulting solid was stirred, filtered and washed with methanol (100 ml). The solid was dried at 65° C. to obtain anhydrous bosentan Form C (85 gms).

Example 7 i) Bosentan Barium 5 gms of p-tert-butyl-N-[6-chloro-5-(O-methoxy-phenoxy)[2,2'-bipyrimidin]-4-yl]benzenesulfonamide potassium salt and barium hydroxide (0.75 gms) were charged to a reaction vessel. Ethylene glycol (15 ml) and toluene (75 ml) were added thereto. The reaction mass was heated at a temperature of 110° C. for 2 hours. Further, 0.75 gms of barium hydroxide was added and heating was continued for another 4 hours. After completion of the reaction, the resulting solid was filtered and isolated as barium salt of bosentan. It was further purified by crystallizing with a mixture of methanol and isopropyl acetate. (Yield: 3 gms)

ii) Bosentan Form B 100 gms of barium salt of bosentan obtained from step i) was charged to a reaction vessel along with a mixture of water and dichloromethane (1:1). The pH of the reaction mass was adjusted to 1-2 using 1:1 HCl and extracted in dichloromethane. The organic layer was collected and washed with water (300 ml) and the solvent was distilled off to obtain a residue. It was further treated with a mixture of ethyl acetate and heptane (1:1). The slurry was stirred at 80° C. to obtain a clear solution. The solution was cooled to 25° C. The solid thus obtained was stirred, filtered and washed with heptane (200 ml). The solid was dried at 65° C. to obtain anhydrous bosentan Form B (60 gms).

Example 8

Bosentan Form B 100 gms of p-tert-butyl-N-[6-chloro-5-(O-methoxy-phenoxy)[2,2'-bipyrimidin]-4-yl]benzenesulfonamide potassium salt and sodium hydroxide (4 gms) were charged to a reaction vessel. Ethylene glycol (300 ml) and toluene (750 ml) were added thereto. The reaction mass was heated at a temperature of 110° C. for 2 hours. Further 10 gms of sodium hydroxide was added and heating was continued for another 2 hours.

After completion of the reaction, toluene was removed by distillation and water (300 ml) was added. The pH of the reaction mass was adjusted to 1-2 with 1:1 HCl and extracted in dichloromethane. The organic layer was collected and washed with water (300 ml) and the solvent was distilled off to obtain a residue. The residue was treated with a mixture of ethyl acetate:heptane (1:1) and heated at 80° C. to obtain a clear solution. The solution was cooled to 25° C. The resulting solid was stirred, filtered and washed with heptane (200 ml). The solid was dried at 65° C. to obtain anhydrous bosentan Form B (40 gms).

Example 9 i) Bosentan Barium 5 gms of p-tert-butyl-N-[6-chloro-5-(O-methoxy-phenoxy)[2,2'-bipyrimidin]-4-yl]benzenesulfonamide potassium salt and barium hydroxide (0.75 gms) were charged to a reaction vessel. Ethylene glycol (15 ml) and toluene (75 ml) were added thereto. The reaction mass was heated at a temperature of 110° C. for 2 hours. Further, 0.75 gms of barium hydroxide was added and heating was continued for another 4 hours. After completion of the reaction, the resulting solid was filtered and isolated as the barium salt of bosentan. The solid was further purified by crystallizing with a mixture of methanol and isopropyl acetate. (Yield: 3 gms)

ii) Bosentan Form C 50 gms of barium salt of bosentan obtained from step i) was charged to a reaction vessel along with mixture of water and dichloromethane (1:1). The pH of the reaction mass was adjusted to 1-2 using 1:1 HCl and extracted in dichloromethane. The organic layer was collected and washed with water (150 ml) and the solvent was distilled off to obtain a residue. It was further treated with methanol (500 ml). The slurry was stirred at 60-65° C. to obtain a clear solution. The solution was cooled to 25° C. The solid thus obtained was stirred, filtered and washed with methanol (50 ml). The solid was dried at 65° C. to obtain anhydrous bosentan Form C (40 gms).

Example 10

Bosentan Form C 100 gms of p-tert-butyl-N-[6-chloro-5-(O-methoxy-phenoxy)[2,2'-bipyrimidin]-4-yl]benzenesulfonamide potassium salt and sodium hydroxide (4 gms) were charged to a reaction vessel. Ethylene glycol (300 ml) and toluene (750 ml) were added thereto. The reaction mass was heated at a temperature of 110° C. for 2 hours. Further 10 gms of sodium hydroxide was added and heating was continued for another 2 hours. After completion of the reaction, toluene was removed by distillation and water (300 ml) was added. The pH of the reaction mass was adjusted to 1-2 with 1:1 HCl and extracted in dichloromethane. The organic layer was collected and washed with water (300 ml) and the solvent was distilled off to obtain a residue. The residue was treated with methanol (1000 ml) and heated at 60-65° C. to obtain a clear solution. The solution was cooled to 25° C. The resulting solid was stirred, filtered and washed with methanol (100 ml). The solid was dried at 65° C. to obtain anhydrous bosentan Form C (82 gms).

Example 11

Bosentan Form A 50 gms of p-tert-butyl-N-[6-chloro-5-(O-methoxy-phenoxy)[2,2'-bipyrimidin]-4-yl]benzenesulfonamide potassium salt and calcium hydroxide (4 gms) were charged to a reaction vessel. Ethylene glycol (150 ml) and toluene (380 ml) were added thereto. The reaction mass was heated at a temperature of 110° C. for 2 hours. Further 5 gms of calcium hydroxide was added and heating was continued for another 2 hours. After completion of the reaction, toluene was removed by distillation and water (150 ml) was added. The pH of the reaction mass was adjusted to 1-2 with 1:1 HCl and extracted in dichloromethane. The organic layer was collected and washed with water (150 ml) and the solvent was distilled off completely to obtain a residue. The residue was further treated with 50 ml of diethyl ether, stirred to obtain uniform solid which was filtered and dried at 85° C. to obtain amorphous bosentan Form A (35 gms).

Example 12

Bosentan Form A

A solution of bosentan in dichloromethane (5 gms of bosentan in 50 ml of dichloromethane) was stirred at 25° C. to 30° C. for about 15 minutes. The solution was concentrated slowly by heating at a temperature of 45° C. to 50° C. to obtain a foamy residue. The residue was further treated with 50 ml of heptane, stirred to obtain a uniform solid which was filtered and dried at 85° C. to obtain amorphous bosentan Form A (4.8 gms).

Example 13

Bosentan Form B

Amorphous bosentan Form A (10 gms) was treated with a mixture of ethyl acetate: heptane (1:1). The reaction mass was stirred at 80° C. to obtain a clear solution. The solution was cooled to 25° C. The resulting solid was stirred, filtered and washed with heptane (50 ml). The solid was dried at 65° C. to obtain anhydrous bosentan Form B (6 gms).

Example 14

Bosentan Form C

Amorphous bosentan Form A (10 gms) was treated with methanol (100 ml). The reaction mass was stirred at 60-65° C. to obtain a clear solution. The solution was cooled to 25° C. The resulting solid was stirred, filtered and washed with methanol (25 ml). The solid was dried at 65° C. to obtain anhydrous bosentan Form C (8 gms).

It will be appreciated that the invention may be modified within the scope of the appended claims.

What is claimed is:

1. Anhydrous bosentan.
2. Anhydrous bosentan according to claim 1, in polymorphic Form C.
3. Anhydrous bosentan Form C according to claim 2, characterised by having an XRPD pattern with peaks at 9.3, 15.2, 15.5, 16.7, 18.6 and 22.7° 2θ±0.2° 2θ.
4. Anhydrous bosentan Form C according to claim 2, characterised by having an XRPD pattern with peaks at 9.3, 15.2, 15.5, 16.7, 18.6, 20.3, 21.3 and 22.7° 2θ±0.2° 2θ.
5. Anhydrous bosentan Form C according to claim 2, characterised by having the XRPD pattern as shown in FIG. 4.
6. Anhydrous bosentan Form C according to claim 2, characterised by having a DSC thermogram as shown in FIG. 5.
7. Anhydrous bosentan Form C according to claim 2, characterised by having an IR spectrum as shown in FIG. 6.
8. An alkaline earth metal salt of bosentan.
9. The salt of bosentan according to claim 8, wherein the salt is the barium salt or the calcium salt.
10. A process for preparing bosentan or a salt thereof comprising coupling p-tert-butyl-N-[6-chloro-5-(2-methoxy-phenoxy)-[2,2'-bipyrimidin]-4-yl]benzenesulfonamide or a salt thereof with ethylene glycol in the presence of a base selected from an alkaline earth metal hydroxide.
11. The process according to claim 10, wherein the p-tert-butyl-N-[6-chloro-5-(2-methoxy-phenoxy)-[2,2'-bipyrimidin]-4-yl]benzenesulfonamide is in the form of the potassium salt.
12. The process according to claim 10, wherein the base is barium hydroxide or calcium hydroxide.
13. The process according to claim 10, wherein the base is present in a sub-molar quantity.
14. The process according to claim 10, wherein the coupling is carried out in the presence of a non-polar solvent.
15. The process according to claim 14, wherein the solvent is selected from diglyme, tetrahydrofuran, 2-methyltetrahydrofuran, toluene or xylene.
16. The process according to claim 10, wherein the product of the coupling step is isolated to form an alkaline earth metal salt of bosentan.
17. The process according to claim 10, wherein the product of the coupling step is converted to bosentan, the conversion comprising adding water to the reaction mass of the coupling step and adjusting the pH of the solution to a value ranging from 1 to 2 using an aqueous solution of HCl.
18. The process according to claim 10, wherein the bosentan is isolated by extracting the crude bosentan using an extraction solvent selected from dichloromethane, ethyl acetate and toluene, adding an antisolvent and isolating the precipitated bosentan.
19. The process according to claim 18, wherein the antisolvent is selected from: methanol; ethanol; isopropanol; butanol; a mixture thereof with water; or a mixture of N,N-dimethylformamide and water.
20. The process according to claim 19, wherein the antisolvent is a 1:1 mixture of ethanol and water.
21. A process for preparing anhydrous bosentan Form C, the process comprising refluxing bosentan in methanol, cooling the solution to a temperature below 50° C. whereby the anhydrous bosentan Form C precipitates.
22. The process according to claim 21, wherein the precipitated bosentan Form C is isolated and dried at a temperature above 60° C.
23. Anhydrous bosentan in polymorphic Form B.
24. Anhydrous bosentan Form B according to claim 23, characterised by having an XRPD pattern comprising peaks at 9.6, 16.1, 17.1, 18.4 and 21.8° 2θ+0.2° 2θ.
25. Anhydrous bosentan Form B according to claim 23, characterised by having an XRPD pattern comprising peaks at 9.6, 12.3, 14.8, 16.1, 17.1, 17.5, 18.4, 21.1, 21.8, 22.1 and 22.8° 2θ+0.2° 2θ.
26. Anhydrous bosentan Form B according to claim 23, characterised by having the XRPD pattern as shown in FIG. 1.
27. Anhydrous bosentan Form B according to claim 23, characterised by having a DSC thermogram as shown in FIG. 2.
28. Anhydrous bosentan Form B according to claim 23, characterised by having an IR spectrum as shown in FIG. 3.
29. A process according to claim 18, wherein the antisolvent is selected from: tetrahydrofuran; heptane; n-hexane; and methanol, the mixture of the bosentan and antisolvent is heated to the reflux temperature of the solvent mixture, the mixture is cooled to 25° C., the precipitated product is isolated and the product is anhydrous bosentan Form B.
30. A process according to claim 29, wherein the mixture of the bosentan and antisolvent is heated to the reflux temperature of the solvent mixture, then cooled to a temperature ranging from 20° C. to 30° C. whereby the anhydrous bosentan Form B precipitates.
31. A process according to claim 29, wherein the precipitated bosentan Form B is isolated and dried at a temperature above 60° C.
32. A process for preparing anhydrous bosentan Form B, the process comprising adding bosentan to a mixture of a solvent and an antisolvent, heating the mixture to the reflux temperature of the solvent mixture and cooling the mixture to a temperature ranging from 20° C. to 30° C. whereby the anhydrous bosentan Form B precipitates.
33. A process according to claim 32, wherein the solvent is selected from dichloromethane, ethyl acetate or toluene.
34. A process according to 32, wherein the antisolvent is selected from tetrahydrofuran, heptane, n-hexane, and methanol.
35. A process according to claim 32, wherein the precipitated bosentan Form B is isolated and dried at a temperature above 60° C.

* * * * *

UNITED STATES PATENT AND TRADEMARK OFFICE
CERTIFICATE OF CORRECTION

PATENT NO.       : 8,481,730 B2
APPLICATION NO. : 12/811279
DATED            : July 9, 2013
INVENTOR(S)      : Rao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 199 days.

Signed and Sealed this
Eighth Day of September, 2015

Michelle K. Lee
*Director of the United States Patent and Trademark Office*